bolovan et al.

United States Patent [19]
Spector et al.

[11] Patent Number: 5,922,328
[45] Date of Patent: Jul. 13, 1999

[54] METHODS AND COMPOSITIONS FOR TREATMENT OF HSV-2 INFECTIONS AND CONDITIONS

[75] Inventors: Frances C. Spector, Mountain View, Calif.; Bernard Roizman, Chicago, Ill.; Richard Spaete, Belmont, Calif.

[73] Assignee: Aviron, Mountain View, Calif.

[21] Appl. No.: 08/709,004

[22] Filed: Sep. 6, 1996

Related U.S. Application Data

[60] Provisional application No. 60/003,502, Sep. 11, 1995.

[51] Int. Cl.$^6$ .................. A61K 39/245; A61K 39/12; A01N 63/00
[52] U.S. Cl. ..................... 424/231.1; 424/205.1; 424/204.1; 424/199.1; 424/93.2; 424/93.6; 435/236
[58] Field of Search ............... 424/199.1, 204.1, 424/205.1, 231.1, 93.2, 93.6; 435/236

[56] References Cited

U.S. PATENT DOCUMENTS 5,328,688   7/1994   Roizman .................... 424/205.1

OTHER PUBLICATIONS

Bolovan et al. J. Virol. 68(1): 48–55, 1994.
Laure Aurelian "Herpes Simplex Viruses" In: Encyclopedia of Virology, vol. II, Webster and Granoff, eds., Academic Press Limited, London, pp. 5878–5593, 1994.
Whitley, Replication, Establishment of Latency, and Induced Reactivation of Herpes Simplex Virus γ1 34.5 Deletion Mutants in Rodent Models, *J Clin Invest 91*: 2837–43 (1993).
Kehm, In Vitro Expression of UL56 Gene of Herpes simplex Virus Type 1, *Virus Res 33*: 55–66(1994).
Meignier, In Vivo Behavior of Genetically Engineered Herpes Simplex Viruses R7017 and R7020, *J Inf Dis 162*: 313–21(1990).
Nash & Spivack, The UL55 and UL56 Genes of Herpes Simplex Virus Type 1 Are Not Required for Viral Replication, Intraperitoneal Virulence, or Establishment of Latency in Mice, *Virology 204*: 794–98(1994).
Inglis, Challenges and Progress in Developing Herpesvirus Vaccines, *Tibtech* vol. 13, pp. 135–142 (Apr. 1995).
Chou, Mapping of Herpes Simplex Virus 1 Neurovirulence to γ1 34.5, a Gene Nonessential for Growth in Culture, *Science 250*: 1262–66(1990).
McGeoch, Comparative Sequence Analysis of the Long Repeat Regions and Adjoining Parts of the Long Unique Regions in the Genomes of Herpes Simplex Viruses Types 1 and 2, *J Gen Virol 72*: 3057–75(1991).

*Primary Examiner*—Lynette F. Smith
*Assistant Examiner*—Jay F. Williams
*Attorney, Agent, or Firm*—Luann Cserr; Tracy Dunn

[57] ABSTRACT

A live, attenuated HSV-2 virus and methods of making and using the virus are provided. The live, attenuated HSV-2 virus is constructed using recombinant techniques and can be used in a pharmaceutical composition for prophylactic treatment of HSV-2 infections and for treatment of recurrent HSV-2 related diseases and conditions. Additionally, a plasmid vector is disclosed for expressing a GST-UL56 fusion protein wherein the protein comprises the Glutathione S Transferase gene product fused to at least an immunogenic portion of the HSV-2 UL56 gene product. The GST-UL56 fusion protein can be used to produce polyclonal antisera to the HSV-2 UL56 gene product, to detect whether recombinant HSV-2 deletion mutants express UL56, and as a type-specific reagent capable of discerning HSV-1 from HSV-2.

7 Claims, 9 Drawing Sheets

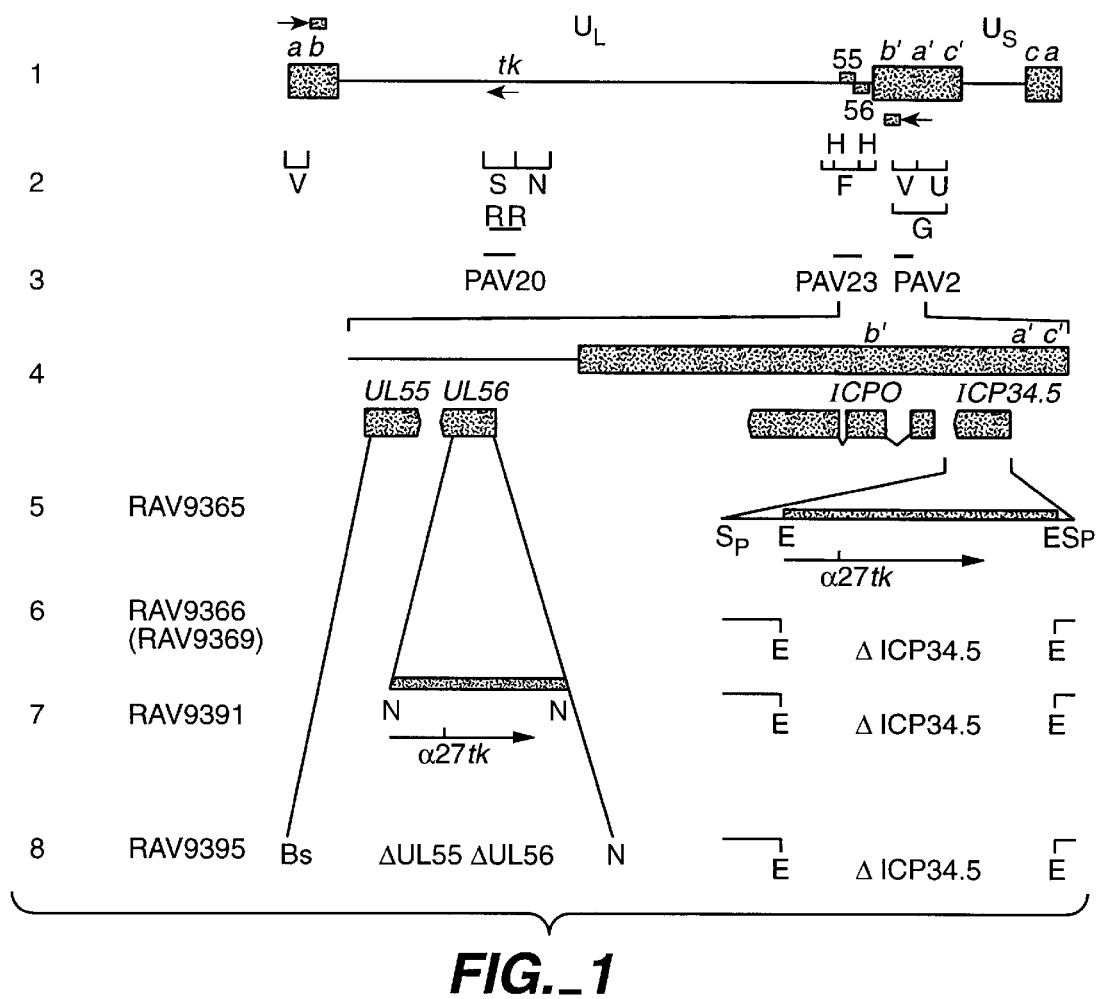
FIG._1

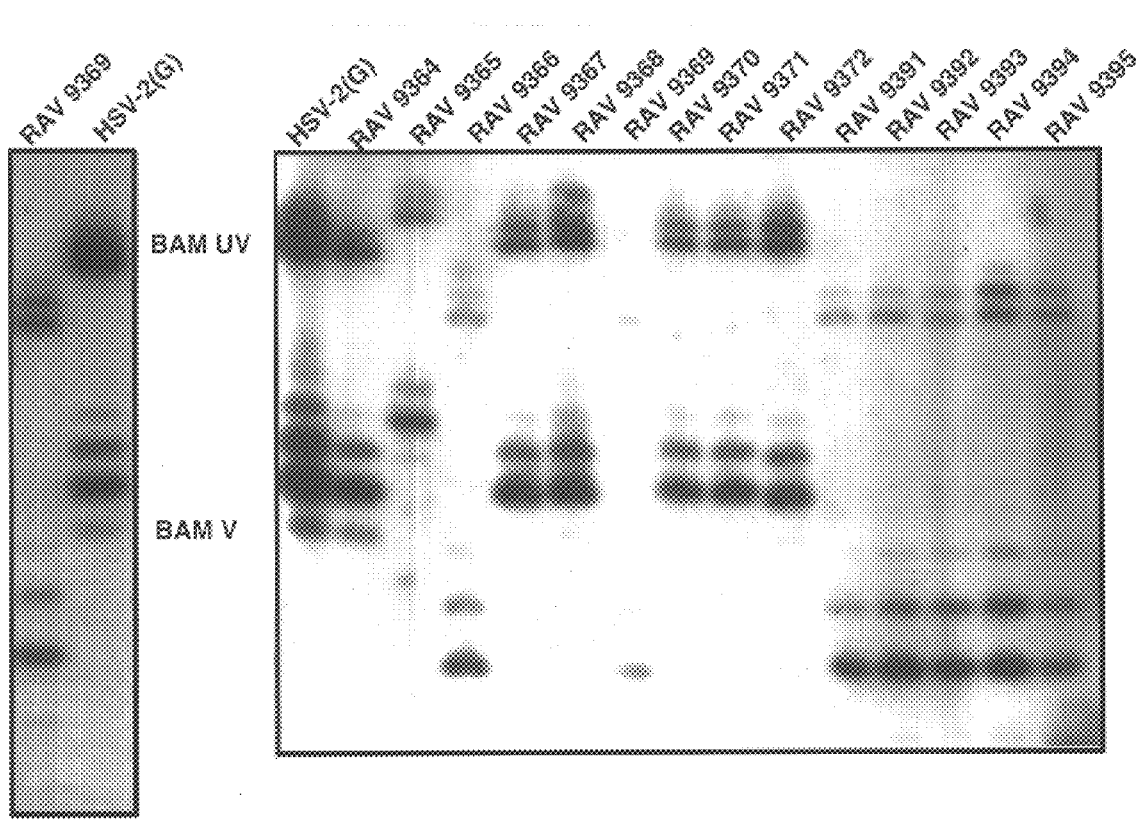
FIG._2A-1
FIG._2A-2

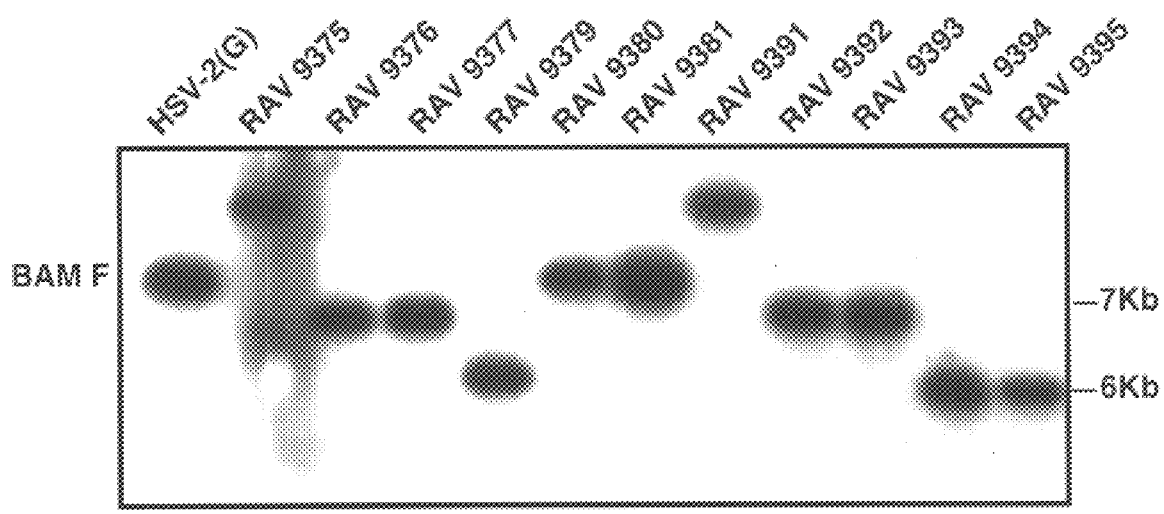
FIG._2B

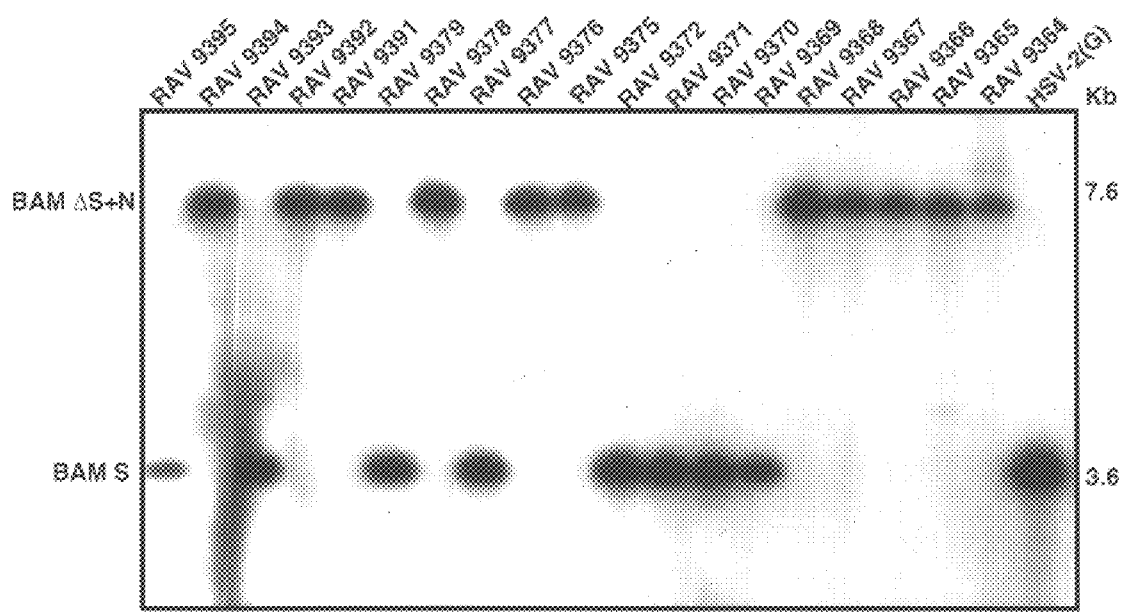
FIG._2C

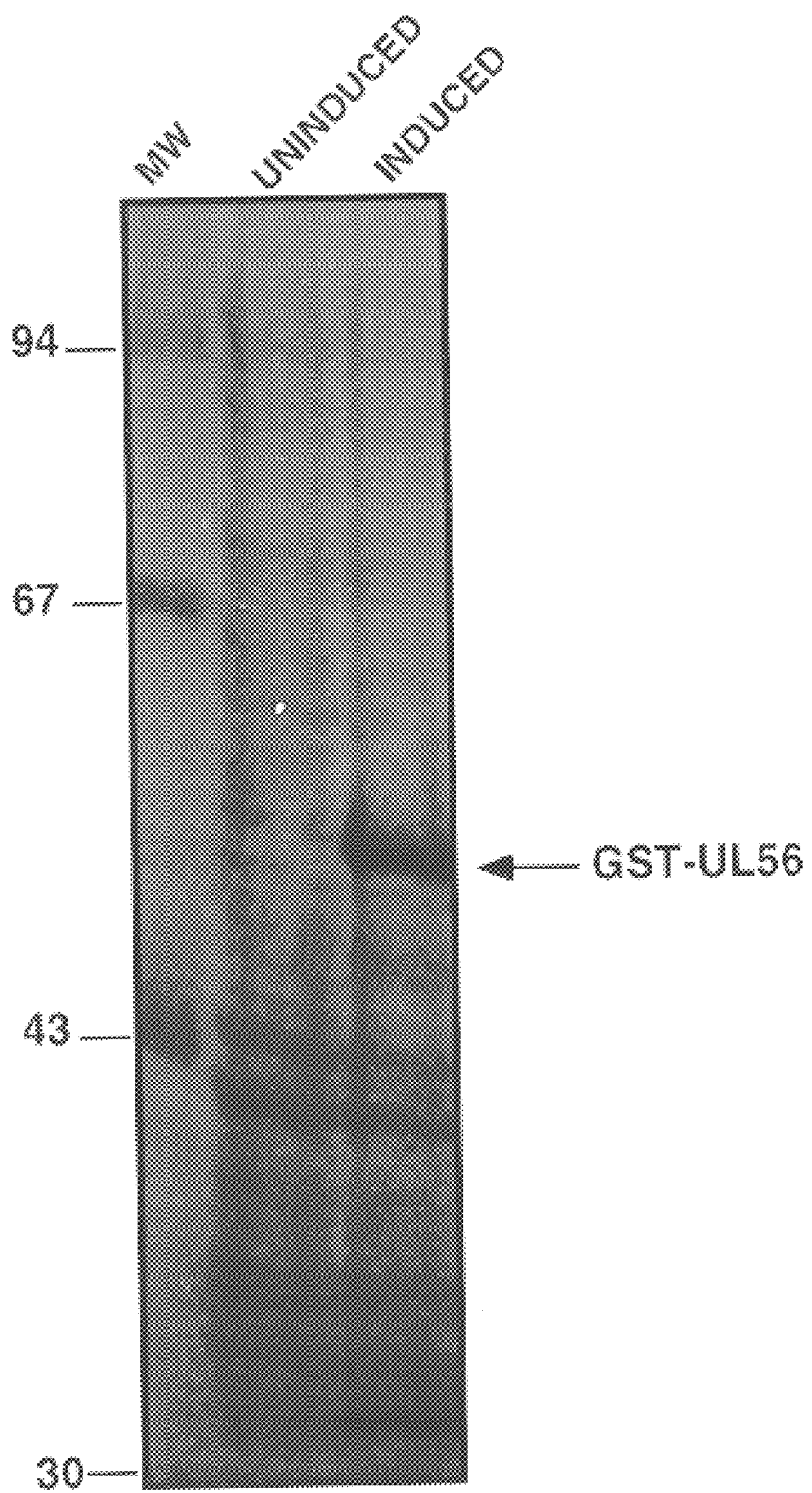
FIG._3A

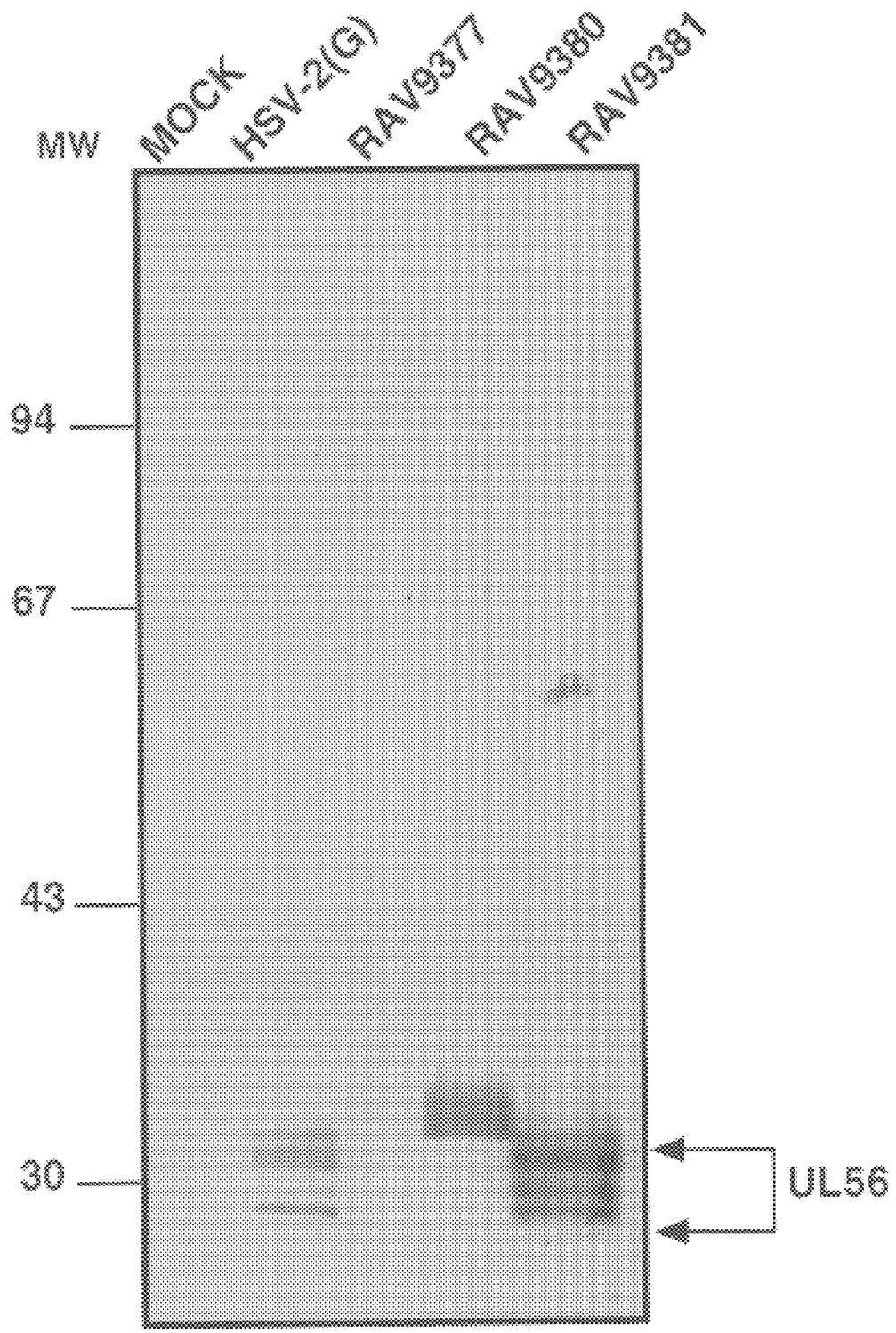
FIG._3B

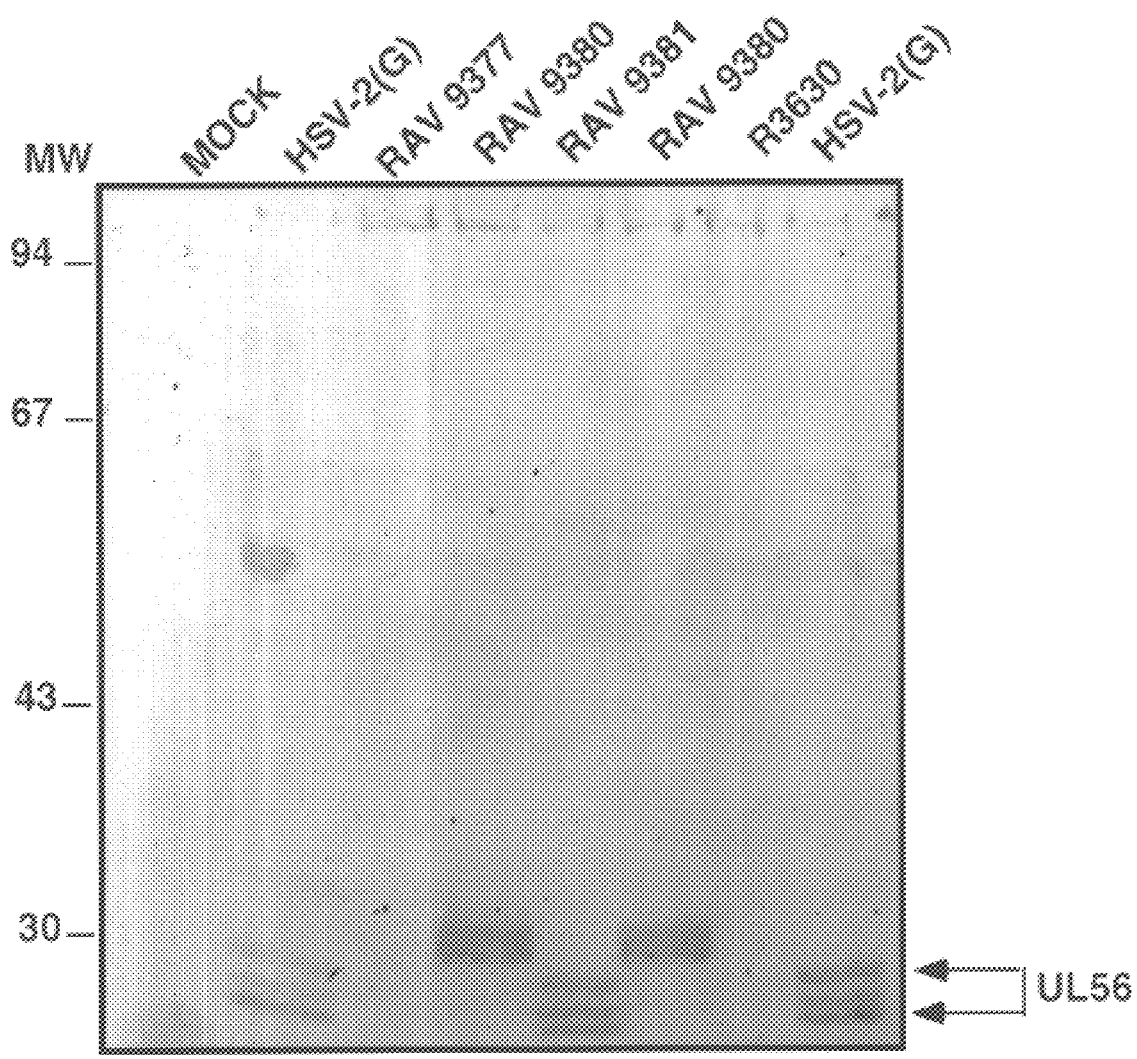
FIG._3C

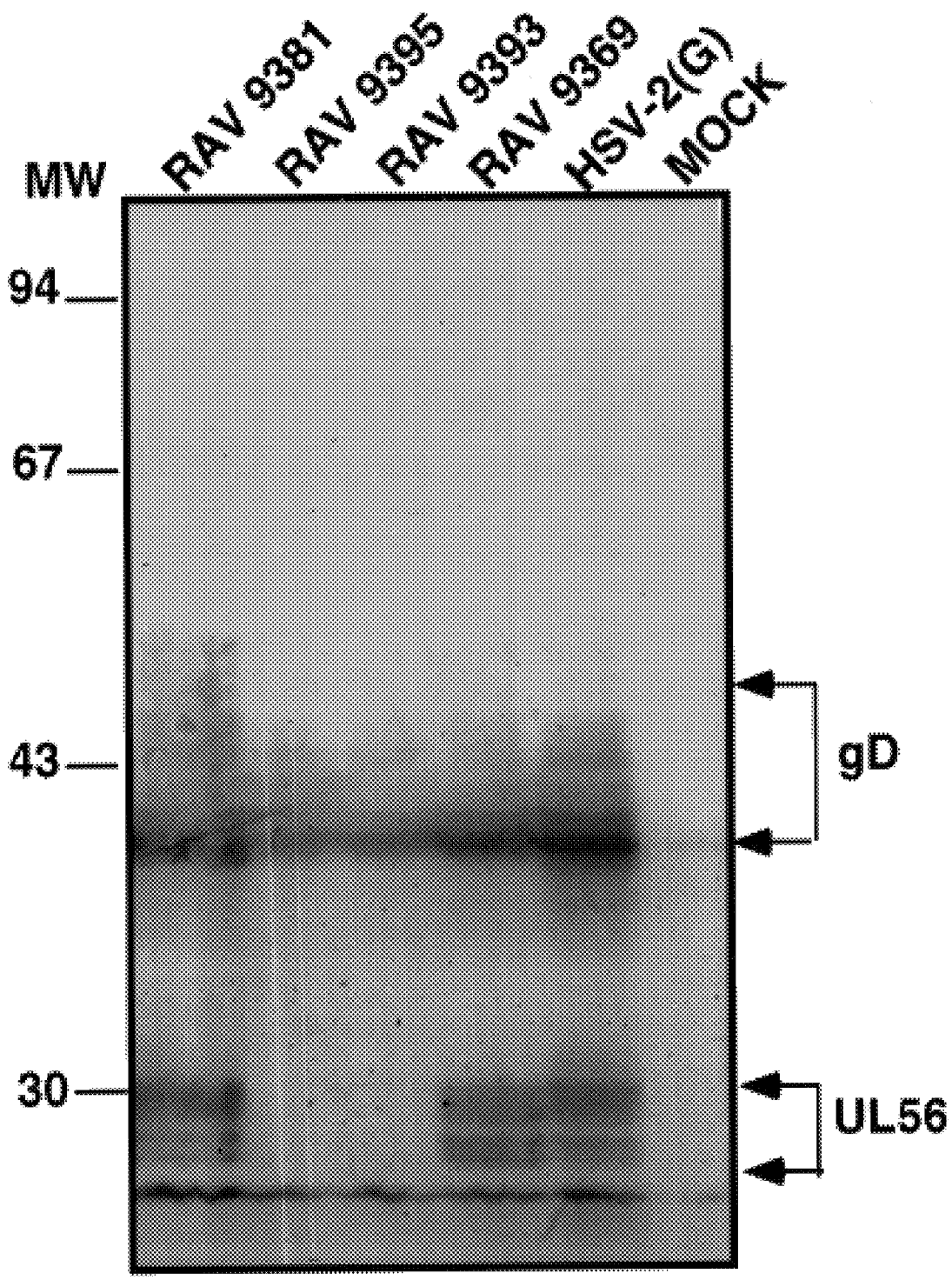
FIG._3D

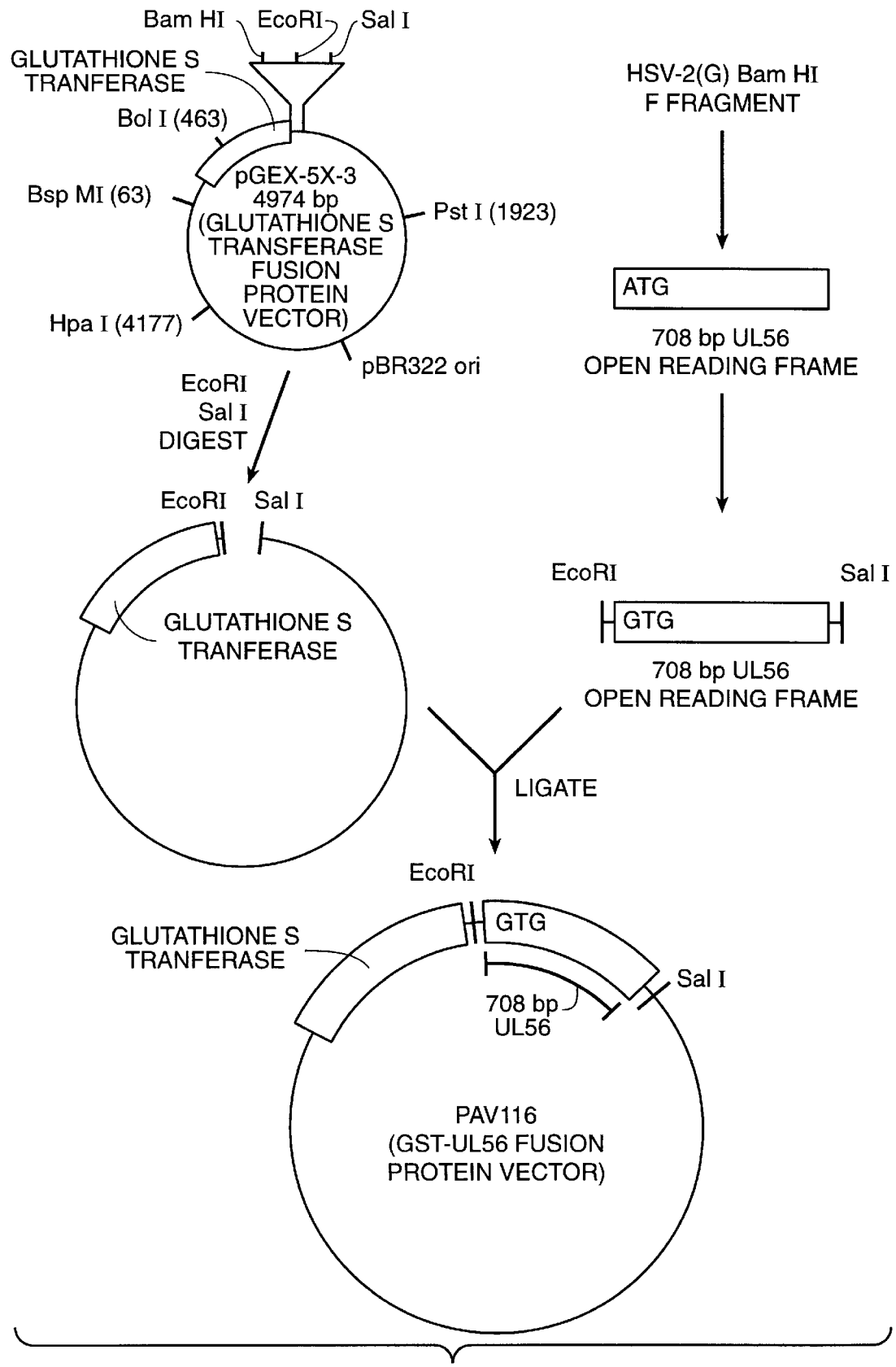
FIG._4

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 18 amino acids
      (B) TYPE: amino acid
      (D) TOPOLOGY: linear (ii) MOLECULE TYPE: protein (xi) SEQUENCE DESCRIPTION: SEQ ID NO:1:

Met Ala Leu Gly Ala Gly His Ala His Ala Cys Arg Asp Asp Gly Asp Asp

-continued

```
                 1               5                   10                  15
Ser (2) INFORMATION FOR SEQ ID NO:2:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Leu Gly Ala Gly His Ala His Ala Cys Arg Asp Asp Gly Asp Asp
1               5                   10                  15
Ser (2) INFORMATION FOR SEQ ID NO:3:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:3:

Arg Ala Ala Trp Arg Ala Ala Arg Arg Ala Arg Arg Arg Ala Glu Arg Arg
1               5                   10                  15
Ala (2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: protein (xi) SEQUENCE DESCRIPTION: SEQ ID NO:4:

Arg Ala Ala Trp Arg Ala Ala Arg Arg Ala Arg Arg Arg Ala Glu Arg Arg
1               5                   10                  15
Ala
```

METHODS AND COMPOSITIONS FOR TREATMENT OF HSV-2 INFECTIONS AND CONDITIONS

BACKGROUND

This application hereby claims benefit of priority, based on co-pending Provisional Application 60-003,502, filed Sep. 11, 1995.

Herpes Simplex Viruses types 1 and 2 (HSV-1 and HSV-2) are two members of the family Herpesviridae, which is defined by the architecture of the virion. B. Roizman, "Herpesviridae: A Brief Introduction" in Fields Virology, 2d ed., Vol. 2, pp. 1787–1793 (B. N. Fields and D. M. Knipe, eds. 1990). HSV-1 and HSV-2 are both members of the subfamily called the Alphaherpesvirinae, both are grouped in the E class of genome structure of the viruses comprising the family Herpesviridae, and both have a genome size of 152 kilobase pairs. HSV-1 and HSV-2 are closely related and have strong similarities in genome structure and at the nucleotide level. See McGeoch et al., J. Gen. Virol. 72:3057–3075 (1991). HSV-1 and HSV-2 are distinguishable in several aspects, including their G+C content of 67 mole % and 69 mole %, respectively. Also, the sequences in the HSV-1 and HSV-2 $R_L$ regions are more divergent than in the $U_L$ and $U_S$ regions. McGeoch et al., J. Gen. Virol. 72:3057–3075 (1991). HSV-1 and HSV-2 also differ in retriction enzyme cleavage sites and in the sizes of viral proteins. Roizman & Sears, "Herpes Simplex Viruses and Their Replication" in Fields Virology, 2d ed., Vol. 2, pp. 1795–1817 (B. N. Fields and D. M. Knipe, eds. 1990).

HSV-1 infections are extremely common and affect from 70–80 percent of the total population in the United States. HSV-1 is transmitted via oral secretions, respiratory droplets or direct oral contact, and results in lesions or blisters on the mouth and lips. HSV-2 is transmitted venereally and causes ulcers and lesions on the genitals and surrounding areas, which can result in urinary retention, neuralgia and meningoencephalitis.

There are many HSV-2 viral strains currently known, including HSV-2 strains G, HG52, and 333. The nucleotide sequences encompassing UL55, UL56 and a proposed ICP34.5 of HSV-2 strain HG52 have been sequenced. McGeoch et al., J. Gen. Virol. (1991). A restriction map for the HSV-2 strain HG52 has also been published in Chartrand, et al., J. Gen. Virol. 52:121–133 (1981), which is incorporated herein by reference. The HSV-2 strains G and 333 have the same BamHI, BspEI, EcoRI and Hind III restriction maps in the locale of the tk gene. The HSV-2 HG52 and G strains also have the same NcoI and BsgI restriction maps in the locale of the UL55 and UL56 genes. In the locale of the proposed HSV-2 ICP34.5 gene, HSV-2 strains HG52 and G have very similar EcoO109I and SphI restriction sites. The HSV-2 virus includes all viral strains that have been classified as HSV-2 by the Herpesvirus Study Group of the International Committee on the Taxonomy of Viruses (ICTV). See. e.g., Roizman B et al., Herpesviridae, Definition, provisional nomenclature and taxonomy in Intervirology 16:201–217 (1981).

HSV-2, like other herpesviruses, has the ability to establish both a primary and a latent infection in its host. During the primary infection, HSV-2 infects the skin and epithelial cells and then spreads to the ganglia of the peripheral nervous system. After the lesions from the primary infection have healed, the HSV-2 viral DNA can remain dormant in the ganglia. This dormant or inert state is referred to as a state of latency. Periodically, the HSV-2 can become reactivated and cause lesions around the initial site of infection. During the recurrent disease episodes, the infectious HSV-2 virus particles are shed from the lesions. From a clinical perspective, this recurrence of HSV-2 infection is particularly problematic because it can occur up to ten times per year, can cause severe physical and psychological discomfort and creates the risk of infecting the patient's sexual partners. In certain individuals, recurrent infections may be asymptomatic, which can lead to inadvertent HSV-2 infection of others.

The number of individuals infected with HSV-2 in the United States is estimated to range from 40 to 60 million, and from 0.5 to 1 million new cases of genital herpes are diagnosed annually in the United States. See R. Whitley and J. Gnann, "The Epidemiology and Clinical Manifestations of Herpes Simplex Virus Infections" in The Human Herpesviruses, pp. 69–105 (Roizman, B., R. J. Whitley and C. Lopez eds. 1993). HSV-2 infection worldwide continues to increase.

Two groups that suffer the most severe forms of herpetic diseases caused by HSV-2 are infants or immunocompromised individuals. HSV-2 infection of neonates can result in encephalitis, skin lesions, keratoconjunctivitis, widely disseminated infections, microcephaly or hydranencephaly. Neonatal HSV-2 infection is almost always symptomatic and frequently lethal.

Currently, the major therapeutic treatment for recurrent HSV-2 infections is administration of acyclovir, which reduces the duration and severity of primary infection as well as the frequency of recurrence, but does not prevent asymptomatic viral shedding or the establishment of latency.

The high incidence of HSV-2 infection, recurrent disease episodes, and asymptomatic transmission suggest that the best treatment will be a prophylactic treatment capable of preventing or ameliorating HSV-2-related diseases or conditions.

A number of different approaches to the development of HSV vaccines have been attempted, including live, attenuated HSV viruses, live virus vectors, killed virus vaccines and subunit protein vaccines. See R. L. Burke, "Current Status of HSV Vaccine Development" in The Human Herpesviruses, pp. 367–379 (B. Roizman, R. J. Whitley, and C. Lopez eds. 1993). A live virus vaccine is distinguishable from a killed virus vaccine in that the live virus is able to replicate, whereas the killed virus preparations are inactivated with phenol, formaldehyde, heat or ultraviolet light and are unable to replicate. Thus, the term "live" when used to describe a virus means that it is capable of replication. An attenuated virus is one that does not cause physical signs of disease and reduces person-to-person dissemination. An attenuated virus may still be capable of establishing latency. The advantage of a live, attenuated HSV-2 virus vaccine is that the live, attenuated HSV-2 virus can present a range of viral antigens to the host and stimulate both cell-mediated and humoral immune responses, which are both important in protection against HSV-2-related diseases and conditions. See S. C. Inglis, "Challenges and progress in developing herpesvirus vaccines," Tibtech vol. 13, pp. 135–142 (April 1995). Attempts at producing an effective HSV-2 subunit vaccine have been unsuccessful to date.

Two of the most comprehensively developed live, attenuated HSV vaccines are recombinant derivatives of HSV-1 strain F, called R7017 and R7020. Meignier et al., J. Infect. Dis., 158:602–614 (1990). R7020 consists of the HSV-1 strain F genome having selected deletions and insertions. Results of human vaccine trials with R7020 indicate that while it is extremely safe, it is over attenuated for purposes of eliciting immunological protection against HSV-2 in humans.

Little is known about the functions of the UL55 and UL56 gene products, except that they appear to be nonessential genes and do not share any sequence homology suggesting functional similarity. Nash & Spivack, Virology 204:794–798 (1994). The sequence of the UL55 and UL56 genes of HSV-2 strain HG52 has been described by McGeoch, J. Gen. Virol. 72:3057–3075 (1991) and is incorporated herein by reference. The UL56 gene of HSV-1 strain F has been cloned and expressed to produce recombinant polypeptides that are immunoreactive with antibodies in human HSV-1 IgM-positive sera. Kehm et al., Virus Research 33:55–56 (1994).

The HSV genome contains two copies of the $\gamma_1 34.5$ nucleotide sequence that encodes the Infected Cell Protein 34.5 ("ICP34.5"). (The terms $\gamma_1 34.5$ and ICP34.5 are used interchangeably throughout this application. The term "nucleotide sequence" is used to denote the polynucleotide.) There is one $\gamma_1 34.5$ nucleotide sequence in each of the inverted repeats flanking the long unique sequence of HSV-1. Chou et al., Science 250:1262–1266 (1990). A proposed sequence of ICP34.5 in HSV-2 strain HG52 has been disclosed. McGeogh, J. of Gen. Vir. 72:3057–3075 (1991), which is herein incorporated by reference. The ICP34.5 nucleotide sequence is predicted to encode a protein of 261 amino acids. In contrast, the HSV-1 ICP34.5 sequence is predicted to encode a protein of 263 amino acids. Thus, there remains a need in the art for a live, attenuated viral composition for the prophylactic treatment of HSV-2.

BRIEF SUMMARY OF THE INVENTION

As one aspect, a live, attenuated HSV-2 virus is provided. The live, attenuated HSV-2 virus of the invention can also be referred to as a recombinant HSV-2 virus or an HSV-2 deletion virus or an HSV-2 mutant. One embodiment of the live, attenuated HSV-2 virus is characterized by having both copies of the ICP34.5 nucleotide sequence deleted; the UL56 nucleotide sequence deleted; and a portion of the UL55 nucleotide sequence deleted. Preferably, the portion of UL55 that is deleted from the live, attenuated HSV-2 virus of the invention is that sequence extending from the BsgI site located 102 base pairs from the UL55 start codon to the end of the UL55 coding sequence. The invention includes any HSV-2 strain that has at least a single base pair deletion or mutation in all of the following: both copies of the ICP34.5 nucleotide sequence, the UL55 nucleotide sequence and the UL56 nucleotide sequence, preferably the deletions are at least 100 bases long and in the coding region. The mutations in each of the ICP34.5, UL55 and UL56 nucleotide sequences usually have the effect of altering the amino acid composition of the resulting polypeptides or disrupting the expression of the full polypeptide or completely inactivating expression of these polypeptides. The recombinant HSV-2 virus comprises mutations of the ICP34.5, UL55 or UL56 genes that are modified by insertion, deletion, nucleic acid substitution or deletion, or by insertion of a codon that stops translation of the gene, in order to detrimentally affect virulence while retaining the immunogenic character of HSV-2.

This live, attenuated HSV-2 virus offers several advantages over the known live, attenuated HSV viruses developed for prophylactic treatment of HSV: (1) the deletions were selectively chosen to avoid over attenuation of the HSV-2 virus such that the resulting virus would be efficacious for prophylactic treatment of HSV infections and conditions as well as safe; (2) the deletion of the coding sequence for the ICP34.5 protein was selected to ensure replication incompetence in the central nervous system; and (3) the use of HSV-2 rather than HSV-1 as the parent virus ensured an appropriate cytotoxic T lymphocyte response to infection by HSV-2. The parent virus from which the live, attenuated viruses of the invention are derived can be any HSV-2 strain. Many strains of HSV-2 have been isolated. Few HSV-2 strains have been sequenced, but many have been analyzed for restriction fragment length polymorphisms. These strains are largely conserved at the nucleotide level.

As another aspect, a method is provided for making a live, attenuated HSV-2 virus comprising providing an isolated HSV-2 virus; mutating a portion of each of the two copies of the $\gamma_1 34.5$ nucleotide sequence; mutating a portion of the UL56 nucleotide sequence; and mutating a portion of the UL55 nucleotide sequence. The portions of the $\gamma_1 34.5$, UL55 and UL56 nucleotide sequences that are to be mutated range from any single base pair to the full nucleotide sequences, including any intermediate-size deletions or mutations that result in attenuation of the HSV-2 virus. The mutations to be introduced usually have the effect of altering any polypeptides expressed from the $\gamma_1 34.5$, UL55 and UL56 nucleotide sequences, compared to the corresponding polypeptides expressed from the parent HSV-2 strain. The portion of the UL55 nucleotide sequence to be mutated preferably comprises a deletion of at least the nucleotide sequence from the BsgI site located 102 base pairs from the start codon to the end of the UL55 nucleotide sequence in any HSV-2 strain having the same BsgI restriction site at position 102 as that of the HSV-2 HG52 strain, including HSV-2(G) and HSV-2 strain 333.

As yet another aspect of the invention, an isolated polypeptide is provided, comprising a fusion protein having at least an immunogenic portion of an HSV-2 UL56 polypeptide fused to a Glutathione S Transferase (GST) polypeptide, wherein the GST polypeptide is at the amino terminus of the fusion protein and the HSV-2 UL56 polypeptide portion is at the carboxyl terminus of the fusion protein. The GST-UL56 fusion polypeptide that contains the entire UL56 polypeptide fused to a full GST polypeptide is approximately 52 kilodaltons. However, the GST-UL56 fusion proteins of the invention can contain smaller portions of the UL56 polypeptide that are immunogenic and therefore can be expected to be smaller than 52 kD. These GST-UL56 fusion proteins are useful for many purposes, including confirming whether recombinant HSV-2 viruses express UL56, developing polyclonal antisera or monoclonal antibodies specific to epitopes of the HSV-2 UL56 protein; and developing an immunoassay to detect the expression of HSV-2 UL56 in a sample. The GST-UL56 fusion proteins of the invention can also be used as a type-specific reagent capable of discerning HSV-1 from HSV-2.

As a further aspect of the invention, a plasmid is described that expresses a fusion protein comprising at least an immunogenic portion of the HSV-2 UL56 polypeptide and the Glutathione S Transferase (GST) polypeptide. The plasmid of the invention comprises an HSV-2 UL56 nucleotide sequence comprising at least a sequence encoding an immunogenic portion of the HSV-2 UL56 polypeptide up to and including the entire 708 base pair HSV-2 UL56 nucleotide sequence. This UL56 nucleotide sequence is inserted into the pGEX5.3 GST fusion protein vector such that the UL56 open reading frame is in frame with the GST open reading frame. The plasmid of the invention also includes a plasmid comprising the entire 708 base pair HSV-2 UL56 open reading frame from the ATG to the stop codon, said entire HSV-2 UL56 reading frame inserted into the pGEX5.3 GST fusion vector, wherein the UL56 open reading frame is in frame with the GST open reading frame. The invention includes a composition comprising a polyclonal antisera generated by immunizing a mammal with an isolated GST-UL56 fusion protein. The polyclonal antisera is useful for assaying for the presence of HSV-2 UL56 in a sample and confirming expression of HSV-2 UL56 in an expression system.

As yet a further aspect, the live, attenuated HSV-2 virus of the present invention may be used in therapeutic and/or immunogenic compositions for preventing and treating HSV related conditions and diseases. The pharmaceutical compositions of the invention can be used for the prophylactic treatment of an HSV-2 related disease or condition and comprises an immunizingly effective amount of a live, attenuated HSV-2 virus described herein in a suitable pharmaceutical vehicle. This pharmaceutical composition can be used to generate a neutralizing immune response to HSV-2 infection, for prophylactic treatment of HSV-2 infection and amelioration of HSV-2 related conditions, and for prevention of recurrent HSV-2 disease symptoms. A human host can be inoculated intramuscularly or subcutaneously with a pharmaceutical composition of the invention comprising an immunity-inducing dose of one or more of the recombinant HSV-2 viruses described herein. Other modes of inoculation include surface scarification or inoculation of a body cavity. Generally, effective immunization of a human host can be achieved by one to several inoculations of between 10 and 1,000,000 pfu each, as measured in susceptible human or nonhuman primate cell lines, preferably 1,000 to 30,000 pfu will be used. The following are exemplary indications for vaccination: (1) a need to boost the host's level of immunity; (2) a lack of immunity combined with a high probability of natural infection; and (3) a lack of immunity and a high likelihood that the subject will become immunocompromised due to immunosuppressive therapy in the near future. The pharmaceutical composition according to the present invention can be used in liquid form or in freeze-dried form with suitable preservatives and protective agents to preserve the viral strains during the freeze drying process.

As still another aspect, a method is described for the prophylactic treatment of a herpes simplex type 2-related disease or condition in a mammal comprising administering an immunizingly effective amount of a pharmaceutical composition to a mammal. The pharmaceutical composition comprises a live, attenuated HSV-2 virus having at least a single base pair deletion or mutation in each of the following: both copies of the ICP34.5 nucleotide sequence, the UL55 nucleotide sequence and the UL56 nucleotide sequence. The deletions or mutations in each of the ICP34.5, UL55 and UL56 nucleotide sequences usually have the effect of altering the amino acid composition of the resulting polypeptides or disrupting the expression of the full polypeptides or completely inactivating expression of these polypeptides. Preferably, the method of prophylactic treatment is designed for human patients with HSV-2-related diseases or conditions.

BRIEF DESCRIPTION OF THE DRAWINGS

FIG. 1 is a schematic diagram showing the genetic organization of RAV 9395 and the other recombinant HSV-2 viruses that were constructed in the process of constructing RAV 9395.

FIG. 2A is a Southern analysis of recombinant HSV-2 viruses en route to recombinant HSV-2 virus RAV 9395.

FIG. 2B is a Southern analysis of HSV-2 recombinant viruses with deletions in the UL55 and UL56 genes, probed with the HSV-2(G) Bam HI F fragment.

FIG. 2C is a Southern analysis of $tk^+$ and $tk^-$ recombinant viruses en route to development of recombinant HSV-2 virus RAV 9395.

FIG. 3A is a Coomassie stained protein gel confirming induction by IPTG of a 52 kD GST-HSV-2 UL56 fusion protein in E. coli.

FIG. 3B is a Western blot showing the use of the polyclonal antiserum raised against the GST-UL56 fusion protein to demonstrate the expression or lack of expression of UL56 in the recombinant viruses leading up to RAV 9395.

FIG. 3C shows a Western blot demonstrating that the polyclonal antiserum raised against the GST-UL56 fusion protein is specific for HSV-2 UL56 and does not specifically bind HSV-1 UL56 polypeptides.

FIG. 3D shows that RAV 9395 does not express the UL56 gene product, via an immunoblot of RAV 9395 infected cell lysates and probing with the polyclonal antiserum raised against the GST-UL56 fusion protein.

FIG. 4 is a diagram depicting the construction of the GST-UL56 fusion protein vector, PAV116.

DETAILED DESCRIPTION OF THE INVENTION

The present invention provides a method of constructing a recombinant HSV-2 virus that is a live, attenuated HSV-2 for use as a prophylactic treatment for HSV-2 infections and HSV-2 related diseases and conditions.

In order to construct the desired recombinant HSV-2 virus, RAV 9395, viral DNA of intermediate recombinant HSV-2 viruses was purified from viral lysates using standard procedures and analyzed by Southern blot, using DNA probes that were labeled with $^{32}P$ using a nick translation kit. In order to confirm whether the recombinant HSV-2 viruses expressed UL56, the 708 bp HSV-2 UL56 open reading frame was cloned from HSV-2 strain G into a fusion protein vector. The UL56 open reading frame was cloned in frame with the Glutathione S transferase fusion protein, and the resulting plasmid, PAV116, was used to transform a bacterial culture. The induction of the GST-UL56 fusion protein was confirmed by SDS polyacrylamide gel electrophoresis followed by coomassie blue staining. The fusion protein was purified by affinity chromatography, and the purified preparation was used to immunize rabbits for production of polyclonal antiserum specific to HSV-2 UL56. After additional booster immunizations with the affinity purified GST-UL56 fusion protein, the presence of UL56-specific antibodies in the rabbit sera was tested using Western blots of HSV-2(G) infected cell lysates probed with the rabbit polyclonal antisera raised against the GSTUL56 fusion protein.

In order to assay the recombinant HSV-2 viruses for expression of UL56, the viruses were grown on cell monolayers that were harvested and lysed. The proteins were separated in denaturing polyacrylamide gels and transferred to nitrocellulose using well-known procedures. After blocking treatment, the nitrocellulose blots containing proteins expressed by the cells infected by the recombinant HSV-2 viruses, were incubated with the rabbit polyclonal antiserum raised against the GST-UL56 fusion protein. Bound rabbit antibodies were detected by using goat anti-rabbit IgG conjugated to alkaline phosphatase and substrates Nitro blue tetrazolium and 5-bromo-4-chloro-3-indolyl for a colorimetric reaction.

The recombinant HSV-2 virus RAV 9395 was constructed through a series of insertions and deletions to the HSV-2 strain G. RAV 9395 has the entire UL56 nucleotide sequence, both copies of the ICP34.5 nucleotide sequence, and a portion of the UL55 nucleotide sequence deleted. In order to construct the recombinant HSV-2 virus, RAV 9395, the parent strain, HSV-2 (G) was used. A series of insertions and deletions using selection for thymidine kinase was conducted according to the procedure described by Post and Roizman, Cell 25:227–232 (1981). This procedure allows the introduction of site-specific mutations or deletions that are introduced by co-transfection with a deletion or insertion plasmid that contains flanking nucleotide sequences that recombine with the co-transfected parent viral strain to be altered.

The live, attenuated HSV-2 vaccine candidate, designated RAV 9395, had the following nucleotide sequences deleted from the HSV-2(G) parent strain: (1) a 1033 bp deletion in each of the two ICP34.5 nucleotide sequences, the deletions stretching from the EcoO109I site located 16 bp from the start codon of the ICP34.5 open reading frame to the EcoO109I site located 110 bp after the stop codon of the ICP34.5 open reading frame; and (2) a deletion from the NcoI site at the start codon of the UL56 gene to the BsgI site located 102 bp from the start codon of the UL55 open reading frame. These deletions comprised a 923 bp deletion in both copies of the ICP34.5 nucleotide sequence and all of the UL56 nucleotide sequence and approximately the last 458 bp of the UL55 gene. RAV 9395 contains an intact, functional tk gene.

Using the methods described herein, other recombinant HSV-2 viruses can be constructed having a range of mutations or deletions in both copies of the ICP34.5 nucleotide sequence, the UL55 nucleotide sequence, and the UL56 nucleotide sequence.

The RAV 9395 recombinant HSV-2 virus was used to immunize intramuscularly *Aotus trivirgatus* sp. monkeys with varying doses, ranging from $10^3$, $10^4$, $10^5$, and $10^6$ plaque forming units (pfu). The Aotus monkey is exquisitely sensitive to HSV-infection and is therefore an animal model that closely approximates the neonate. Thirty days after immunization, the monkeys were challenged with $10^2$ pfu of wild type HSV-2 (G), which is normally a lethal dose. All animals survived the challenge, and all three animals immunized with the $10^3$, $10^4$, and $10^5$ pfu doses of RAV 9395 showed no disease symptoms and only some weight loss. The animal receiving the $10^6$ pfu dosage of RAV 9395 exhibited some discharge at the injection site, some weight loss, and some isolated lesions at distant sites. The animal tolerated these lesions well and later recovered completely. Because the Aotus monkey is exquisitely sensitive to HSV infection, these results show that RAV 9395 is a promising candidate for a safe and effective prophylactic treatment of HSV-2 infection in humans. Based upon well-known techniques for calculating dosages and immunization protocols, the RAV 9395 as well as the range of recombinant HSV-2 viruses described herein can be used in a pharmaceutical composition for both the prophylactic treatment of HSV-2 infection as well as treatment for recurrent HSV-2 disease symptoms and conditions.

The live, attenuated HSV-2 virus and the methods and products of the present invention are further described in the following examples, which are intended to illustrate the invention without limiting its scope.

EXAMPLES

Example 1

Materials and Methods

Cells and viruses.

$Tk^+$ and $tk^-$ viruses were selected in human 143TK- cells. Hep-2, Vero, MRC-5, 10T1/2 and SK-N-SH neuroblastoma cell lines were used for protein analyses and growth characteristics of the recombinant viruses constructed in this study. All cells lines except MRC-5 and 10T1/2 were maintained in minimum essential medium (MEM) (JRH Biosciences, Lenexa, Kans.) supplemented with 10% fetal calf serum (FCS) (JRH Biosciences, Lenexa, Kans.), L-glutamine (2 mM), penicillin (100 units/ml), streptomycin (0.1 mg/ml) and pyruvate (1 mM). MRC-5 cells were maintained in Dulbecco's modified Eagle's medium (DME) (JRH Biosciences, Lenexa, Kans.) plus 10% FCS and supplemented as above. 10T1/2 cells were maintained in basal Eagle's medium (BME) (Sigma, St. Louis, Mo.) plus 10% FCS and supplemented as above. Prior to experimentation all cells were transferred to DME plus 10% FCS. For selection of $tk^+$ viruses, this medium was supplemented with $1.1\times10^{-4}$M hypoxanthine, $4.5\times10^{-7}$M aminopterin and $2\times10^{-5}$M thymidine (HAT) (Sigma, St Louis, Mo.) and for $tk^-$ virus selection, the medium was supplemented with 40 mg/ml of bromodeoxyuridine (BUdR) (Sigma, St Louis, Mo.). Infections were performed in a volume of 1 ml on T25 dishes. The virus inoculum was allowed to adsorb for 1 hour at 37° C., removed and the infected cell monolayers were overlayed DME containing 1% FCS and incubated at 37° C. To pick plaques, the overlay media was supplemented with human immune globulin (Miles, Elkart, Ind.) at 0.1 ml/100 ml medium. The recombinants were routinely plaque purified twice under selection on 143 cells and twice on Vero cells.

Reagents and plasmids.

Restriction enzymes were obtained from New England BioLabs, Beverly, Mass. T4 DNA polymerase and ligase were obtained from Boehringer Mannheim Biochemicals, Indianapolis, Ind. Oligonucleotides were supplied by the Aviron Core facility and were synthesized on an ABI 392 instrument (Applied Biosystems, Foster City, Calif.).

Purification and analyses of viral DNA.

Viral DNA intended for transfections was prepared from NaI (J. T. Baker Inc, Phillipsburg, N.J.) gradients according to the method of Walboomers and Ter Schagget 1976. (A new method for the isolation of herpes simplex virus 2 DNA. Virology 74: 256–258.) Briefly, three roller bottles of Vero cells were infected at approximately 1 plaque forming unit (pfu)/cell with the appropriate recombinant virus. The virus was then propagated at 34° C. for 48 hours till the cytopathic effect (CPE) was 100%. The infected cells were then shaken into the media and the cells were cetrifuged at low speed to pellet the infected cells. The infected cells were then resuspended in PBS (JRH Biosciences, Lenexa, Kans.) and the nuclei were solubilized by the addition of 0.6% Nonidet P40 (NP40) (Sigma). The cells were incubated on ice for 15 minutes with ocassional vortexing. The nuclei were then removed by centrifugation at 1500 rpm in a Beckman bench centrifuge. The supernatant containing the viral DNA was removed and EDTA (Sigma), proteinase K (Boehringer Mannheim), and sodium dodecyl sulfate (SDS) (Sigma) were added to final concentrations of 25 mM, 100 mg/ml and 0.5% respectively. The DNA solution was incubated for at least 1 hour at 37° C. before being loaded on to a 40 ml gradient of saturated NaI containing 6 mg/ml Ethidium Bromide. The gradients were centrifuged at 45,000 rpm overnight in a Beckman VTi50 rotor. The DNA was harvested from the gradient and the ethidium was removed by 3 extractions with isoamyl alcohol. The DNA solution was extensively dialysed against at least 4 changes of 0.01 M Tris and 0.01 M EDTA (TE). The first dialysis solution also contained 100 mM NaCl to facilitate the removal of iodine from the DNA. For small scale preparations, viral DNA was purified by phenol-chloroform extraction of cytoplasmic fractions of infected Vero cells. The viral DNA was analyzed by the method of Southern. Viral DNA was digested with restriction enzymes according to the manufacturer's specifications and the DNA fragments were electrophoretically separated on 0.8% agarose gels containing Tris phosphate buffer (1XTPE) by standard techniques (Maniatis et al., 1982). The separated fragments were then transferred to Hybond-N+ nylon membranes (Amersham Corp.), in the presence of 20XSSC (3 M NaCl, 0.3 M sodium citrate) and immobilized using a UV Crosslinker 1000 (Hoefer Scientific Instruments, San Francisco, Calif.). The membrane with the immobilized DNA fragments was then hybridized to $^{32}$p radiolabeled, denatured DNA probes overnight at 65° C. in a mixture of 0.6 M NaCl, 50 mM sodium citrate (pH7.0), 0.1% SDS, 100 mg/ml of denatured salmon sperm DNA (Boehringer Mannheim), 0.02% Ficoll (type 400-DL; Sigma), 0.02% polyvinylpyrolidone and 0.02% bovine serum albumin (fraction V). The blot was washed four times in an excess volume of a solution containing 60 mM NaCl, 20 mM sodium citrate (pH 7.0), and 0.1% SDS for 15 minutes at 65° C. The DNA probes were radiolabeled with $\alpha[^{32}P]$ dCTP by nick translation according to manufacturer specifications of a kit designed for this purpose (Du Pont, Wilmington, Del.).

Expression of UL56 as a GST fusion protein.

The entire 708 base pair (bp) UL56 open reading frame from the ATG to the stop codon was amplified by polymerase chain reaction (PCR) from the HSV-2(G) BamHI F fragment with linkers containing 5' EcoRI and 3' Sal I restriction enzyme sites appropriate for cloning into the pGEX-5X-3 GST (Glutathione S transferase) fusion protein vector (Pharmacia, Piscataway, N.J.; see Studier, et al., Methods in Enzymology, 135:60) at the EcoRI and SalI sites in the polylinker of the vector. The ATG start codon of the 708 bp UL56 insert was changed to GTG. The amplified product was cloned in frame with the GST protein resulting in clone PAV116. FIG. 4 depicts the construction of PAV116, the GST-UL56 fusion protein expression vector. The GST-UL56 fusion protein was subsequently expressed by induction of a bacterial culture transformed with PAV116 using 1 mM IPTG (Sigma) for two hours. The induction of the predicted 52 kilodalton (kDa) fusion protein was checked by SDS polyacrylamide gel electrophoresis followed by staining with coomassie blue stain. This GST-UL56 fusion protein is characterized by having the GST polypeptide portion at the amino terminus of the fusion protein and the HSV-2 UL56 polypeptide portion at the carboxyl terminus of the fusion protein. This approximately 52 kDa fusion protein was purified by affinity chromatography with glutathione cross linked to agarose beads (Pharmacia). The purity of the preparation was checked by separation on denaturing polyacrylamide gels followed by staining with coomassie blue. The affinity purified preparation was used to immunize rabbits for the production of polyclonal antiserum. Another preparation of SDS polyacrylamide gel purifed GST-UL56 protein was used to further boost the rabbits following the initial immunization.

Production of rabbit polyclonal antisera.

Briefly, two New Zealand rabbits were immunized with a cocktail of two synthetically produced hydrophilic peptides identified on the basis of hydrophilicity as defined by Kyte & Doolittle analysis of the predicted amino acid sequence of the HSV-2 HG52strain UL56 gene. One of the peptides, (SEQ ID NO: 1) Met-Ala-Leu-Gly-Ala-Gly-His-Ala-His-Ala-Cys-Arg-Asp-Asp-Gly-Asp-Asp-Ser, was conjugated to KLH (keyhole limpet hemocyanin), forming (SEQ ID NO: 2) KLH-Met-Ala-Leu-Gly-Ala-Gly-HisAla-His-Ala-Cys-Arg-Asp-Asp-Gly-Asp-Asp-Ser. The other peptide, (SEQ ID NO: 3) Arg-Ala-Ala-Trp-Arg-Ala-Ala-Arg-Arg-Ala-Arg-Arg-Arg-Ala-Glu-Arg-Arg-Ala, was conjugated to MAP (multiple antigen peptide), forming (SEQ ID NO: 4) (Arg-Ala-Ala-Trp-Arg-Ala-Ala-Arg-Arg-Ala-Arg-Arg-Arg-Ala-Ala-Glu-Arg-Arg-Ala)8-MAP. After four immunizations with these peptides, no antibodies to HSV-2 UL56 were detected by enzyme-linked immunosorbent assay (ELISA) in which the peptides described above were used as the capture antigens. The rabbits were then rested for several weeks while the GST-UL56 fusion protein was prepared. The rabbits were immunized three times with affinity purified GST-UL56 fusion protein material and the presence of anti-HSV-2 UL56 antibodies in the rabbit sera were assayed by Western analyses of HSV-2 (strain G)-infected cell lysates. Lysates obtained from cells infected with RAV 9377, a recombinant HSV-2 virus derived from the HSV-2 G strain with a deletion in the UL56 gene stretching from the NcoI site at the ATG start codon of UL56 to the NeoI site at amino acid 150, and lysates of cells infected with RAV 9380, a recombinant HSV-2 virus derived from HSV-2 G with an epitope tag inserted in the UL56 gene product were included in the Western assay as negative and positive controls for signal specificity. The epitope tag was from the α4 gene of HSV-1 which is recognized by monoclonal antibody H943 (all as described by Chou & Roizman, J. Virol. 64:1014 (1990)). Upon detection of antibodies specific for the UL56 gene product, the rabbits were bled and were then boosted with additional GST-UL56 fusion protein material and bled periodically to obtain higher titer sera.

Polyacrylamide gel electrophoresis and immunoblotting.

Vero cell monolayers were infected with the appropriate virus at a multiplicity of infection (mol) of 5 and at 17 hours post infection the cells were harvested. The infected cell monolayers were washed, scraped into cold PBS and centrifuged to pellet the cells. The cell pellets were disrupted by addition of 350 ml of PBS A* ( Phosphate buffered saline containing 1% NP40, 1% Sodium deoxycholate, 10 mM TPCK [Tosylsulfonyl phenylalanyl chloromethyl ketone], 10 mM TLCK [aTosylL-lysine chloromethyl ketone], 5 mM phenylmethylsulfonyl fluoride, 1 mg/ml pepstatin, and 17 mg/ml aprotinin). The proteins were electrophoretically separated in denaturing 10% polyacrylamide gels and the separated polypeptides were transferred to nitrocellulose according to the method of Towbin et al. (1979. Proc. Natl. Acad. Sci. USA 76: 4350–4354). Proteins were electroblotted in 50 mM Tris, 380 mM glycine, 20% methanol (pH 8.3) for 90 min 300 mA. Following transfer, the membrane was immersed in blocking buffer (5% skim milk in PBS) to block for 1 hour at room temperature or overnight at 4° C. The membrane was then washed briefly with a solution containing 1% BSA (bovine serum albumin) in PBS and incubated with the rabbit polyclonal antiserum for 1 hour at room temperature or overnight at 4° C. The membrane was washed in the blocking solution three times for 30 minutes and the bound rabbit antibodies were then detected by incubation of the membrane for 1 hour at room temperature with goat anti-rabbit IgG conjugated to alkaline phosphatase (Promega, Madison, Wis.). The membrane was then washed once with the blocking buffer and three more times with PBS and then developed with the substrates Nitro blue tetrazolium (NBT) and 5-bromo-4-chloro-3-indolyl (BCIP) (both from Promega, Madison Wis.). The reaction was stopped after 10 min by rinsing the membrane in a solution containing 100 mM tris pH 7.6 and 10 mM EDTA.

Example 2

Construction and Description of RAV 9395

Construction of recombinant HSV-2 viruses.

The intermediate recombinant HSV-2 viruses constructed prior to the recombinant HSV-2 virus, RAV 9395, and their genotypes and phenotypes are shown in Table 1. To exploit procedures for the construction of recombinant HSVs by insertion and deletion of a tk selectable marker as described elsewhere (Post and Roizman, Cell 25:227–232 (1981)), a HSV-2 (G) tk$^-$ recombinant was first constructed. This recombinant, designated RAV 9364, was similar to HSV-1 (F) Δ305 (Post et al., Cell 24:555–565 (1981)) in that it was tk$^-$ and the plaques formed by RAV 9364 were syncytial, suggesting that the UL24 open reading frame on the strand opposite the tk gene (encoded by UL23) was also deleted. Jacobson et al., J. Virol. 63:1839 (1989). RAV 9364 served as the parent virus for all the recombinants constructed in this study.

Recombinant virus RAV 9364 is a genetically engineered deletion virus lacking a 498-bp BspEI fragment in the tk gene. RAV 9364 was constructed by co-transfection of rabbit skin cells with PAV14 (described below) along with intact plaque purified HSV-2 (G) DNA. Following transfection tk$^-$ viruses were selected using BUdR. The 498 bp deletion of the tk coding sequence in RAV 9364 eliminates a BamHI restriction enzyme site and results in the fusion of HSV-2(G) BamHI N (approx. 4 kilobase pairs [kbp]) and BamHI ΔS (approx. 3.2 kbp). See Chartrand et al., J. Gen. Virol. 52:121–133 (1981) (FIG. 1 showing BamHIII restriction map of HSV-2 strain HG52). This resulted in a fusion BamHI fragment of 7.2 kb, designated as BamHIΔS+N.

Recombinant HSV-2 viruses were screened using Southern blots probed with PAV20. This screening detected an increase in size of BamHI S from 3.6 to 7.2 kbp. PAV20 is a plasmid containing BamHI S cloned into pGEM3zf+ (Promega, Madison, Wis.) as a probe.

To construct PAV14, the tk deletion plasmid, HSV-2(G) DNA was restriction enzyme digested with HindIII and the resulting subgenomic fragments were cloned into the HindIII restriction site of pGEM9zf−, a commercially available derivative of pGEM3zf+. The clones were screened with a fragment of the HSV-2(G) tk gene amplified using PCR primers selected on the basis of conserved sequences among herpesvirus tk genes, including HSV-1 and HSV-2 tk genes and in particular, due to its sequence availability, the tk gene of HSV-2 strain 333 (Kit et al., Biochim. Biophys. Acta, 741:158 (1983)), and labeled with $\alpha[^{32}P]$ by nick translation. The clone harboring the HSV-2(G) HindIII H DNA fragment (Chartrand et al. (J. Gen. Virol. (1981)) containing the HSV-2 (G) tk gene was designated PAV6. An EcoRI-HindIII fragment of approximately 3.6 kbp, harboring the tk sequence, was excised from PAV6 and cloned into pGEM9Zf− to generate PAV9. A 498 bp BspEI tk fragment was removed from PAV9 and the resulting clone was designated PAV14. One object of the present invention is to provide a live, attenuated HSV-2 virus that is incapable of replicating in and destroying the CNS tissue, wherein said HSV-2 virus lacks a functional ICP34.5 protein.

To engineer deletions or introduce modifications into the $\gamma_1 34.5$ gene RAV 9365, a recombinant virus was constructed which carried two copies of the HSV-1(F) tk gene driven by the HSV-1(F) α27 promoter (α27tk) inserted in both copies of the $\gamma_1 34.5$ gene within the HSV-2(G) genome. It was constructed by co-transfecting rabbit skin cells with intact RAV 9364 viral DNA and PAV16 which contains the 1.7 kbp α27tk chimeric gene inserted into the $\gamma_1 34.5$ gene contained in the BamHI V fragment within the HSV-2 genome. Following transfection $tk^+$ recombinant viruses were selected. The $tk^+$ recombinant viruses were screened for by the presence of the α27tk gene in BamHI V and BamHI G by Southern hybidization using both nick translated pRB3968 containing α27tk sequences to confirm insertion of the tk gene and with PAV2 (described below) to detect the increase in size of the BamHI V and G by 700 bp due to the insertion. To construct PAV16, a 1620 bp SphI fragment was excised from pRB801, a clone containing the BamHI UV junction fragments of HSV-2 (G) cloned into the BamHI site of pUC8, a commercially available plasmid. The 1620 bp SphI fragment was inserted into the SphI site of PAV1, a derivative of pGEM3Zf+ in which the EcoO109I restriction enzyme site was destroyed by cleavage with EcoO109I, blunt ending with T4 polymerase and religating to generate PAV2. The α27tk chimeric gene was excised from pRB3968 as an NcoI fragment and inserted into PAV2 cleaved with EcoO109I by rendering the vector and the fragment blunt ended with T4 polymerase. The 1.7 kbp α27tk gene replaces 1033 bp of HSV-2(G) sequence including 923 bp of the 939 bp ICP34.5 open reading frame and the resulting plasmid was designated PAV5. To restore flanking sequences for recombination of the chimeric gene into the viral genome, the 2.5 kbp SphI fragment containing the α27tk gene within the ICP34.5 open reading frame was excised from PAV5 by partial digestion and cloned into pRB801 cleaved with SphI. The resulting plasmid was designated PAV16.

Recombinant virus RAV 9366, containing a 923 bp deletion in both copies of the $\gamma_1 34.5$ gene was generated by co-transfecting intact RAV 9365 viral DNA with PAV15. In this PAV15 plasmid, nearly all of the coding sequence of the $\gamma_1 34.5$ gene had been deleted. The recombinant viruses were selected. The expected genomic structure was confirmed by hybridization of electrophoretically separated restriction enzyme digests of viral DNA with radiolabeled PAV2. To construct PAV15, PAV2 was digested with EcoO109I, blunt ended with T4 polymerase and religated to generate PAV3. A 587 bp SphI fragment was excised from PAV3 and cloned into pRB801 cleaved with SphI generating PAV15.

Recombinant virus RAV 9369, was constructed by co-transfection of PAV9 with intact RAV 9366 viral DNA and $tk^+$ viruses were selected, plaque purified and screened for the restoration of BamHI N and S indicating that the tk gene had been restored. To ensure that no additional mutations had occurred in the genome as a result of the manipulations of the virus, the ICP34.5 gene sequences were restored in RAV 9369 to generate recombinant virus RAV 9372.

To design a recombinant virus suitable for a live attenuated vaccine it is possible to over-attenuate the virus and consequently negate its utility as a vaccine. To minimize this possibility, a gradation of additional deletions were introduced into RAV9369. The choice of genes to delete or mutate was based on several observations. 1. R7020 a prototype of a live, attenuated, genetically engineered vaccine for HSV-1 contained deletions in UL55 and UL56. 2.

The avirulent phenotype of HFEM, an HSV-1 based isolate could be abolished by allowing expression of the HSV-1 UL56 gene. Rosen-Wolff et al., Virus Research 20:205 (1991) 3. HSV-2(G) based viruses deleted in UL55 and UL56 showed decreased protein synthesis relative to wild type, indicating possible attenuation. Therefore, deletions in genes UL56 and UL55 were introduced into RAV 9366, generating RAV 9392 and 9394, respectively. The tk gene was repaired in each of RAV 9392 and RAV 9394, generating RAV 9393 and RAV 9395, respectively.

To construct RAV 9393 and RAV 9395, an α27tk chimeric gene from HSV-1(F) was inserted into the UL56 sequences of RAV 9366, the tk⁻ parent virus of RAAV 9369, by co-transfection of RAV 9366 viral DNA with PAV27. Tk+ progeny viruses were selected and plaque purified. Viruses were screened for the insertion of the α27tk gene by a 1.2 kbp increase in HSV-2 (G) BamHI F fragment and the resulting tk⁺ recombinant was designated RAV 9391. RAV 9392, containing a 446 bp deletion in the UL56 gene was constructed by co-transfection of intact RAV 9391 DNA and PAV26 onto rabbit skin cells and selection and plaque purification of tk⁻ viruses. Viruses were screened by Southern analyses for a 446 bp decrease in the BamHI F fragment with PAV23 as a probe. RAV 9394 harbors a 1336 bp deletion in the Bam HI F fragment. The deletion removes the entire UL56 open reading frame and almost all of the UL55 gene except for 102 bp which still remain at the N-terminus of the UL55 open reading frame. RAV 9394 was constructed by co-transfection of RAV 9391 with PAV49. Finally the tk gene was restored by co-transfection of PAV9 with RAV 9392 or RAV 9394 DNA onto rabbit skin cells and selection of tk⁺ viruses RAV 9393 and RAV 9395, respectively.

To construct PAV27, the HSV-2(G) 6848 bp BamHI F fragment was cloned into pGEM3zf+ generating PAV24. A chimeric 1.7 kbp α27tk gene from HSV-1(F) was cloned into PAV24 at the NcoI sites and the resulting clone designated PAV27. PAV24 was digested with NcoI and religated to generate PAV26. PAV49 was generated by digestion of PAV26 with NcoI and BsgI, the vector was rendered blunt ended with T4 polymerase and religated. The 1682 bp HSV-2(G) HindIII O fragment was cloned into pGEM9Zf⁻ generating PAV23 which was used as the probe to screen for recombinant viruses deleted in UL56 and UL55.

Description of RAV 9395

The HSV-2 recombinant virus construct designated as RAV 9395 was specifically designed to eliminate the expression of three herpesvirus proteins, ICP34.5, and the proteins encoded by genes UL55 and UL56. To accomplish this RAV 9395 harbored a 1033 bp deletion encompassing 923 bp of the ICP34.5 gene. It stretched from the EcoO109I site located 16 bp from the start codon (ATG) of the ICP34.5 open reading frame to the EcoO109I site located 110 bp after the stop codon of the ICP34.5 open reading frame. As the ICP34.5 gene is present in two copies in the viral genome, the deletion described above was engineered into both copies of the ICP34.5 open reading frame. Additionally, RAV 9395 also contains a large deletion in the UL56 and the UL55 genes. All of the UL56 gene is deleted and only the first 102 bp of the UL55 gene remain (because the UL55 and UL56 genes are in opposite orientation). The deletion stretches from the NcoI site at the start codon of the UL56 gene and extends to the BsgI site located 102 bp from the start codon of the UL55 open reading frame. All site locations are based on the published sequence of HSV-2 strain HG52. McGeogh et al. (1991) Finally, the tk gene in recombinant virus RAV 9395 is intact and functional.

TABLE 1

Recombinant viruses generated en route to RAV 9395

| VIRUS | GENOTYPE | PHENOTYPE |
| --- | --- | --- |
| HSV-2 (G) | wild type | TK⁺ |
| RAV 9364 | ΔUL23, ΔUL24 | TK⁻ |
| RAV 9365 | ΔUL23, ΔUL24, γ₁34.5i | TK⁺, ICP34.5⁻ |
| RAV 9366 | ΔUL23, ΔUL24, Δγ₁34.5 | TK⁻, ICP34.5⁻ |
| RAV 9369 | Δγ₁34.5 | TK⁺, ICP34.5⁻ |
| RAV 9372 | Δγ₁34.5R | TK⁺, ICP34.5⁺ |
| RAV 9375 | ΔUL23, ΔUL24, UL56i | TK⁺, UL56⁻ |
| RAV 9376 | ΔUL23, ΔUL24, ΔUL56 | TK⁻, UL56⁻ |
| RAV 9377 | ΔUL56 | TK⁺, UL56⁻ |
| RAV 9378 | ΔUL23, ΔUL24; ΔUL55, ΔUL56 | TK⁻, UL55⁻, UL56⁻ |
| RAV 9379 | ΔUL55, ΔUL56 | TK⁺, UL55⁻, UL56⁻ |
| RAV 9380 | ΔUL23, ΔUL24, UL56α4H943epi | TK⁻, UL56α4tag |
| RAV 9381 | ΔUL56R | TK⁺, UL56⁺ |
| RAV 9391 | ΔUL23, ΔUL24, Δγ₁34.5, UL56i | TK⁺, UL56⁻ |
| RAV 9392 | ΔUL23, ΔUL24, Δγ₁34.5, UL56 | TK⁻, ICP34.5⁻, UL56⁻ |
| kAV 9393 | Δγ₁34.5, ΔUL56 | TK⁺, ICP34.5⁻, UL56⁻ |
| RAV 9394 | Δγ₁34.5, ΔUL23, ΔUL24, ΔUL55, ΔUL56 | TK⁻, UL55⁻, UL56⁻, ICP34.5⁻ |
| RAV 9395 | Δγ₁34.5, ΔUL55, ΔUL56 | TK⁺, UL55⁻, UL56⁻, ICP34.5⁻ | i denotes an insertion mutant eg. α27tk insertion; R denotes a repair virus; Δ denotes a deletion virus and α4tag denotes a mutant with an HSV-1α4 epitope tag.

Description of FIG. 1

FIG. 1 is a schematic representation of the DNA sequence arrangement in the genomes of HSV-2(G) and the recombinant viruses en route to the RAV 9395. The following section describes FIG. 1.

Line 1 represents the sequence arrangement of the HSV-2 genome. The filled rectangles represent the internal inverted repeats ab, b'a'c', and ca. The HSV-2(G) a sequence is present in a direct orientation at the two genomic termini and in the inverted orientation at the junction between the long and short components, $U_L$ and $U_S$, respectively. Flanking the internal inverted repeat sequences are the unique sequences (represented by thin lines) of the long and short components of the viral DNA. The hollow, outlined arrows represent the ICP0 and ICP34.5 open reading frames which are present in two copies in the viral genome, in the ab and in the b'a'c' inverted repeats. The solid blocked arrows indicate the UL56 and the UL55 open reading frames respectively. The thin black arrow indicates the position of the thymidine kinase (tk) gene.

At Line 2, the relevant Bam HI fragments are indicated as V, S, N, F, and U. The letter G indicates the BamHI G fragment which is a fusion of the BamHI fragments U and V in the illustrated prototype genome organization. The two letters H indicate the HindIII sites of the HindIII O fragment of HSV-2 (G) which is located within the HSV-2(G) BamHI F fragment. The letters B indicate the BspEI sites within the tk gene which flank the 498 bp fragment which is deleted in all the tk- viruses constructed in this study. The removal of the small BspEI fragment also deletes the BamHI site between the BamHI S and the BamHI N fragments.

Line 3 indicates the viral DNA used as probes for the identification of the recombinant viruses. PAV20 is an HSV-2 BamHI S fragment cloned into pGEM3f+. PAV23 is an HSV-2 HindIII O fragment cloned into pGEM9zf⁻. PAV2 contains a 1620 bp SphI fragment from the HSV-2 BamHI G fragment cloned into pGEM3zf+.

Line 4 shows an expansion of the region of viral DNA showing the positioning and orientation of the UL55, UL56 genes and the genes encoding the ICP0 and ICP34.5 gene products.

Line 5 illustrates the genome organization of RAV 9365. This recombinant virus harbors the 498 bp BspEI deletion in the tk gene and also carries a 1.7 kb α27tk gene inserted in place of the 1003 bp EcoO109I fragment within the 1620 bp SphI fragment in the HSV-2(G) BamHI V and G fragments. E=EcoO109I. Sp=SphI.

Line 6 shows the genome organization of RAV 9366. This recombinant harbors the 498 bp BspEI deletion in the tk gene together with a 1003 bp deletion in the viral genome within HSV-2 BamHI fragments V and G. The resulting deletion virus therefore harbors a 923 bp deletion in both copies of the ICP34.5 gene. Recombinant virus RAV 9369 has the same deletion at the ICP34.5 locus but the BspEI 498 bp fragment has been restored in its genome and the tk gene is functional. E=EcoO109I.

Line 7 illustrates the genome organization of recombinant virus RAV 9391. This recombinant also harbors a 923 bp deletion in both copies of the ICP34.5 gene as indicated and carries a deletion of 498 bp in the tk gene as defmed by the BspEI fragment. RAV 9391 carries an α27tk chimeric gene in place of a 446 bp NcoI fragment within the UL56 gene located in the HSV-2 BamHI F fragment. N=NcoI Line 8 depicts the genome organization of recombinant virus RAV 9395. This virus carries the 1003 bp deletion in the HSV-2 BamHI V and G fragments resulting in a 923 bp deletion in both copies of the ICP34.5 gene. RAV 9395 also carries a 1336 bp deletion within the HSV-2 BamHI F fragment encompassing both the UL56 and the UL55 genes. This deletion encompassing the UL56 and UL55 genes stretches from the NcoI site located at the ATG of the UL56 gene to the BsgI site located 102 bp from the start of the UL55 open reading frame. The 498 bp BspEI fragment is restored at the tk locus and the resulting RAV9395 is therefore tk+ and the tk gene is functional. Bs=BsgI.

Southern analyses of recombinant viruses en route to RAV 9395

FIG. 2A illustrates autoradiographic images of BamHI digests of HSV-2 wild-type and recombinant mutant viral DNAs. Viral DNA digests were electrophoretically separated on 0.8% agarose gels, transferred to Hy-bond nylon membranes, and hybridized with specific radiolabeled probes. The viral DNA in both panels was probed with radiolabelled PAV2 which contains ICP34.5 specific sequences together with flanking sequences. BamHI V (Bam V) and BamHI UV (Bam UV) fragments are shown. The multiple banding pattern obtained is due to the heterogeneity of the viral a sequences which are labelled with this probe.

FIG. 2B illustrates autoradiographic images of wild type and recombinant viral DNA digested with BamHI and electrophoretically separated on 0.8% agarose gels, transferred to Hybond nylon membranes and hybridized with radiolabeled PAV23. PAV23 contains the HindIII O fragment of HSV-2 (G) DNA and hybridizes to the BamHI F fragment which contains the UL55 and UL56 genes. The BamHI F fragment is indicated on the blot.

FIG. 2C illustrates autoradiographic images of BamHI digests of wild type and recombinant viral DNAs electrophoretically separated on 0.8% agarose gels, transferred to Hybond nylon membranes and probed with radiolabelled PAV20, a clone containing sequences from the HSV-2 tk gene and its flanking sequences. BamHI S and the new band at approximately 7.2 kb due to the fusion of BamHI N with the deleted form of BamHI S are indicated.

Example 3

Preparation of RAV 9395 in vero and MRC 5 Cell Lines

High titer stocks of RAV 9395 were prepared by two distinct methods. The choice of method was dependent on the cell line and the choice of cell line was contingent on whether the stock of virus was a research stock or for use as a potential vaccine in humans.

Preparation of high titer RAV 9395 in Vero cells.

Six roller bottle cultures of vero cells were grown to 80% confluency at 37° C. The cultures were then infected with RAV 9395 at an input multiplicity of infectivity (MOI) of 0.001–0.01. The virus was allowed to adsorb for 1 hour at 37° C. and the inoculum was replaced with fresh low serum media (see below). The infected cultures were incubated at 34° C. for 4 days till approximately 100% cytopathic effect (CPE) was observable.

The virally infected cells were then removed from the surface of the plastic bottles by vigerous shaking and the infected cells were sedimented by centrifugation at 2000 rpm for 10 minutes in sterile centrifuge bottles. The resulting supernatant was discarded and the pellet of infected cells was resuspended in 12 mls of a 50:50 mixture of low serum media (minimum essential medium (MEM) (JRH Biosciences, Lenexa, Kans.) supplemented with 1% fetal calf serum (FCS)) (JRH Biosciences, Lenexa, Kans.), L-glutamine (2 mM), penicillin (100 units/ml), streptomycin (0.1 mg/ml) and pyruvate (1 mM)), and sterile skim milk (90 g powdered milk [Carnation] in 1 liter of sterile water and this solution was subjected to 3 rounds of autocalving and cooling before it was added to the low serum media). The virus and cell suspension was the sonicated four to six times for 15 second intervals on ice with 2–5 min periods of cooling on ice between each sonication using a vertical probe sonicator. The virus solution was then aliquoted and shock frozen at −80° C. in an upright Harris freezer. An aliquot of the virus was titered on Vero cells after one freeze thaw cycle. The titers were routinely $1 \times 10^9$–$1 \times 10^{10}$ pfu per ml.

Preparation of RAV 9395 in MRC 5 cells.

Six roller bottle cultures of growing MRC-5 cells were infected with RAV 9395 at a MOI of 0.08. After adsorpton of the virus for 1 hour the inoculum was removed and replaced with fresh media. The infected cells were incubated for 4 days at 34–35° C. on a roller bottle apparatus turning at 0.5 rpm, until the cell layer showed maximum CPE. The culture media was discarded and the infected cell monolayers were washed with Dulbeccos phosphate buffered saline (DPBS). The cells were harvested and dounce homogenized using a tight pestle to thoroughly disrupt the cells. The virus/cell suspension was then stabilized by addition of 10XSPG (2.18M sucrose, 0.038M $KH_2PO_4$, 0.072M $K_2HPO_4$ and monosodium glutamate).

Example 4

Generation of a GST-UL56 Fusion Protein and Antibody.

The outline for the methods for generation of the fusion protein and the polyclonal antibody is located in the Materials and Methods section above.

FIG. 3A is a photographic image of a coomassie blue stained 10% denaturing polyacrylamide gel showing electrophoretically separated proteins from cells transformed with PAV116, a plasmid containing the UL56 gene of HSV-2 cloned in frame with the Glutathione S transferase protein (GST-UL56). Lane 1 indicates the molecular weight standard proteins; lane 2 indicates 100 ug of protein extracted from uninduced cultures of bacteria transformed with plasmid PAV116; lane 3 indicates 100 ug of protein extracted from PAV116 transformed bacteria induced with 1 mM IPTG. The arrow indicates the induced GST-UL56 fusion protein migrating with the expected molecular weight of 52 Kd.

FIG. 3B is a photographic image of a Western blot of lysates of cells infected with the indicated recombinant viruses electrophoretically separated in denaturing gels, transferred to nitrocellulose and reacted with polyclonal anti-UL56 serum. The arrows indicate the UL56 specific signals. RAV 9381 is a repair of RAV 9377 which carries a deletion in the UL56 gene. RAV 9380 is a recombinant virus in which the UL56 open reading frame is tagged with a 17 amino acid epitope from the HSV-1 (F) α4 protein.

This polyclonal antibody is specific for HSV-2 UL56 and this is illustrated in FIG. 3C where there is no reaction from lysates with cells infected with the type 1 based recombinant R3630. As the UL56 gene is deleted in recombinant virus RAV 9395 lysates derived from cells infected with RAV 9395 do not express the UL56 gene product and this is illustrated in FIG. 3D which shows a photograph of an immunoblot of cells infected with RAV9395.

The blot shown in FIG. 3D was also probed with a specific monoclonal antibody to the HSV-2 glycoprotein D (gD) as a control for equal protein loading and infectivity.

Example 5

Safety and Efficacy of RAV 9395 in *Aotus trivirgatus* sp.

Three female *Aotus trivirgatus* sp. were immunized intramuscularly with RAV 9395 at doses of $10^3$, $10^4$ and $10^5$ plaque forming units (pfu), respectively. Thirty days post immunization, the Aotus were challenged intravaginally with a lethal dose of $10^2$ pfu of wild type HSV-2 (G). Although some weight loss was observed, the animals appeared to tolerate the challenge well. In contrast, two female Aotus inoculated intramuscularly with wild type HSV-2 (G) at $10^1$ and $10^2$ pfu, respectively, and without prior immunization with RAV 9395, had to be euthanized at day 14 and day 11.

In addition, one female Aotus was immunized intramuscularly with RAV 9395 at a dose of $10^6$ pfu. The animal exhibited some discharge at the injection site, some weight loss and some isolated lesions at distant sites probably resulting from autoinoculation. The lesions resolved and the animal is otherwise normal. The results of these experiments are summarized in Table 1, below.

The results of the Aotus experiment demonstrate a 5 log margin of safety between RAV 9395 and wild type HSV-2 (G). In addition, these experiments demonstrate the protective efficacy of RAV 9395 as a vaccine candidate in an animal model that is exquisitely sensitive to infection by HSV.

TABLE 2

Safety and Efficacy of RAV 9395 in Aotus Monkeys Following Challenge by HSV-2

| Animal # | Virus | Route/Dose | Result of Immunization | Challenge | Result of Challenge | Date of Euthanization |
|---|---|---|---|---|---|---|
| 418 | RAV 9395 | IM $10^3$ | No lesions - slight weight loss appeared normal | I Vag $10^2$ | slight weight loss normal | |
| 509 | RAV 9395 | IM $10^4$ | No lesions - slight erythema at injection site weight loss | I Vag $10^2$ | slight weight loss normal | |
| 438 | RAV 9395 | IM $10^5$ | slight weight loss | I Vag $10^2$ | slight weight loss normal | |
| 445 | RAV 9395 | IM $10^6$ | Discharge from injection site - some weight loss otherwise normal | Not Done | | |
| 411 | HSV-2(G) | IM $10^1$ titer = 12 | severe lesions viremia moribund | | | Day 14 |

TABLE 2-continued

Safety and Efficacy of RAV 9395 in Aotus Monkeys Following Challenge by HSV-2

| Animal # | Virus | Route/ Dose | Result of Immunization | Challenge | Result of Challenge | Date of Euthanization |
|---|---|---|---|---|---|---|
| 331 | HSV-2(G) | IM $10^2$ pfu | | severe lesions viremia moribund | | Day 11 |

IM = intramuscular inoculation; I Vag = intravaginal inoculation

Example 6

Comparison of RAV 9395 and R7020 in *Aotus trivirgatus* sp.

Meignier et al. *J. Inf. Dis.* 162: 313 (1990) reported an extensive study of the behavior of a recombinant HSV type 1 vaccine candidate R7020, in *Aotus trivirgatus* sp. R7020 consists of the HSV-1 strain F genome with a defined number of internal deletions and insertions. Specifically, R7020 lacks (I) UL55, UL56, (ii) all of the internal inverted repeats of the prototype arrangement in the L component and the portion from the L/S junction to the EcoRl site in the domain of the internal inverted repeat portion of the S component, (iii) 500 bp SacI-BglII fragment from the BamHI Q fragment. Included among the sequences deleted are a portion of UL23, a portion of UL24 and one copy each of α0, γ$_1$34.5, ORF P, ORF O, and one complete copy of the sequences which give rise to the Latency Associated Transcript (LAT). In place of the deleted sequences were inserted (a) a copy of the thymidine kinase gene fused in the correct orientation under the transcriptional control of the α4 gene promoter located in the remaining portion of the inverted repeats, and (b) a DNA fragment encoding the HSV-2(G) glycoproteins G, J, D, I and a truncated part of glycoprotein E. Their report documents the lack of significant side effects when R7020 was given Aotus at doses of $10^7$ pfu by intramuscular or subcutaneous routes. In addition, inoculation with $10^6$ pfu either intravaginally or via the ocular mucosa caused no harm to the animals.

The R7020 HSV recombinant was tested in a Phase I trial in humans (Abstract #341, 1992 ICAAC meeting). In seronegative recipients, the vaccine candidate was well tolerated. In HSV-1(+) seropositive individuals, reactogenicity was observed at the dose of $10^{4.5}$ TCID$_{50}$. Antibody increases were not observed in volunteers who were previously HSV-1(+) seropositive. A weak IgG response to HSV-1, but not to HSV-2, was detected by ELISA in seronegative subjects. Following two doses of R7020 at $10^{5.2}$ TCID$_{50}$, a strong ELISA IgG response was observed to HSV-1 and HSV-2. Neutralizing antibodies to HSV-1 were also observed in some volunteers. The R7020 vaccine candidate was not developed further possibly from a perspective that the candidate was over attenuated.

We have confirmed some of the in vivo characteristics in the Aotus monkey study reported by Meignier et al. When we administered R7020 at $10^6$ pfu intravaginally to one of the monkeys from the same cohort as discussed in Example 4, we observed that the virus was well tolerated at this dose and the monkey exhibited no signs of disease. As also discussed in Example 4, when RAV 9395 was given intramuscularly at $10^6$ pfu however, the animal exhibited some discharge at the injection site, some weight loss and some isolated lesions at distant sites probably resulting from auto-inoculation. The lesions resolved and the animal is otherwise normal. This different response indicates that RAV 9395 is less attenuated than R7020 in the Aotus monkey.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A recombinant HSV-2 virus comprising:

a) a mutation that completely inactivates expression of a functional ICP34.5 polypeptide, said mutation being present in each copy of a ICP34.5 polynucleotide;

b) a mutation that completely inactivates expression of a functional UL56 polypeptide, said mutation being present in a UL56 polynucleotide; and c) a deletion of at least 458 base pairs of an open reading frame in a UL55 polynucleotide, said mutation completely inactivating expression of a functional UL55 polypeptide.

2. The recombinant HSV-2 virus of claim 1, wherein the HSV-2 virus is RAV 9395.

3. A pharmaceutical composition comprising the virus of claim 1 in admixture with a pharmaceutically acceptable carrier.

4. A pharmaceutical composition comprising the virus of claim 2 in admixture with a pharmaceutically acceptable carrier.

5. A method for inducing a protective immune response against Herpes Simplex Type 2 in a mammal comprising administering an immunizing amount of the pharmaceutical composition of claim 3 or 4 to said mammal.

6. The method of claim 5 wherein said mammal is a human.

7. The method of claim 6 wherein administration is by injection and said immunizing amount is between $10^3$ to $10^5$ PFU.

* * * * *